United States Patent [19]

McQuilkin

[11] Patent Number: 4,858,608
[45] Date of Patent: Aug. 22, 1989

[54] APPLICATOR

[75] Inventor: Peter H. McQuilkin, Kimberley, United Kingdom

[73] Assignee: Femcare Limited, Nottingham, United Kingdom

[21] Appl. No.: 88,699

[22] Filed: Aug. 21, 1987

[30] Foreign Application Priority Data

Aug. 23, 1986 [GB] United Kingdom ............... 8620560

[51] Int. Cl.⁴ ............................................. A61B 17/12
[52] U.S. Cl. ............................... 128/325; 227/DIG. 1
[58] Field of Search ............... 128/326, 325, 346, 321, 128/303 A; 227/DIG. 1C

[56] References Cited

U.S. PATENT DOCUMENTS 2,034,785  3/1936  Wappler .............................. 128/321
4,106,508  8/1978  Berlin .............................. 128/325 X Primary Examiner—Michael H. Thaler
Attorney, Agent, or Firm—Salter & Michaelson

[57] ABSTRACT

The applicator is designed for easy assembly the joint being visible to the operator to ensure correct assembly and is provided with means for limiting movement of the operating head to prevent accidental over closure of a sterilization clip during entry.

7 Claims, 4 Drawing Sheets

APPLICATOR

The present invention relates to applicators and more particularly to applicators for use with laparoscopes and for applying a sterilisation clip to a tube to sterilise a patient.

A known applicator comprises first and second parts, the first part comprising an operating handle and the second part the operating head of the applicator. Because of the requirement that the applicator must be operated through the laparoscope the two parts are required to be separable in order that the internal diameter of the laparoscope does not have to be large enough to allow the operating head to pass therethrough. In the known design the two parts are connected by a screw threaded engagement of tubular members in the centre of the laparoscope. There is no substantial difficulty in engagement of the screw threads but the design has a number of disadvantages. Firstly because of the fine nature of the threads there is a possibility of cross-threading leading to damage of the applicator and also to incorrect engagement of the operating levers within the tubular members. This can lead to an incorrect operation of the applicator causing possible incomplete closure of the sterilisation clip thereby leading to failure of the operation.

Additionally the operating levers in the two parts must be joined and are joined by a ball and socket joint to enable the operating handle to both push and pull the levers thereby controlling operation of the head. This ball joint is susceptible to wear because the applicator is continuously being assembled and disassembled for each clip fitted. Such wear can lead to an incomplete closure of a clip and hence failure of the operation.

Also because the alignment of the operating head and handle is determined by the accurate locking of the screw threads then because of wear induced by repeated joining of the two parts the alignment alters and the applicator becomes more difficult to use, again creating the possibility of failure to align and apply the clip correctly.

The existing design of applicator is also weak at the screwed middle joint because the screw threads further reduce the outside diameter plus wall thickness (because the tube is hollow) and can readily be bent thus further exacerbating the problem since the threads become stretched.

It is an object of the present invention to provide an applicator for sterilisation clips which overcomes the disadvantages of the known clip and which has further advantages.

According to the present invention there is provided an applicator for a sterilisation clip the applicator comprising a first portion and a second portion, the first portion including an operational handle and the second portion, including an elongate tube for passage completely through a laparoscope and including means for engageably attaching the first and second portions at the handle end of the laparoscope such that the engagement can be visually checked.

Preferably the engagement is by screw thread means and includes means for locking the alignment of an operating head and the handle. The means for locking the alignment is preferably by shaping the engagement end of the second portion in a manner to engage in a nonrotatable manner a shaped end of the first portion.

The applicator also preferably provides stop means for allowing the operator to partially close the operating head in a positive manner against the stop means to allow the laparoscope and applicator to be fed through a cannula into the interior of a patient.

Embodiments of the present invention will now be described by way of example with reference to the accompanying drawings, in which.

Figure 1:
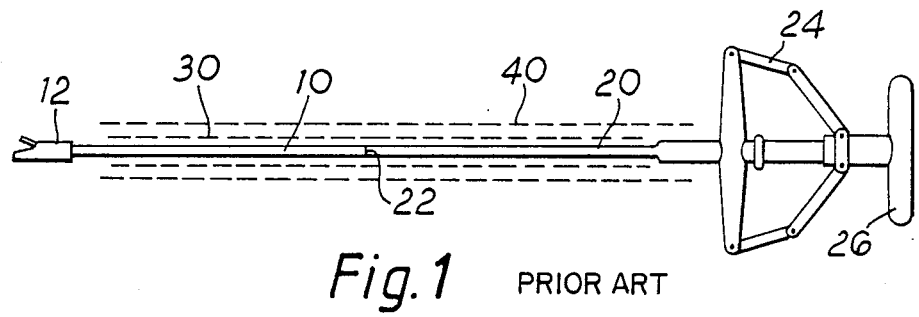
FIG. 1 shows a known applicator.
Figure 2:
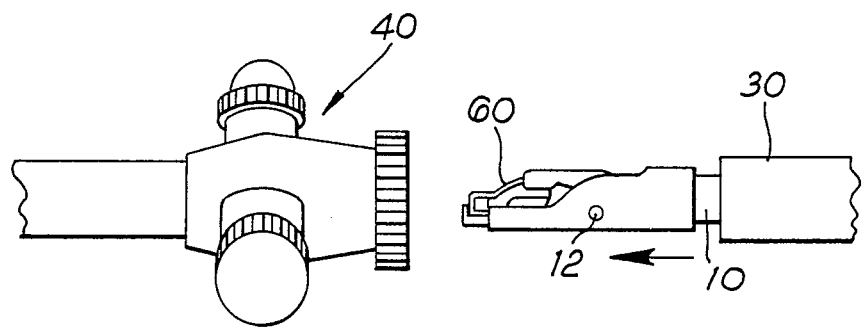
FIG. 2 shows the operating head end of the applicator of FIG. 1 showing the laparoscope and cannula.
Figure 3:
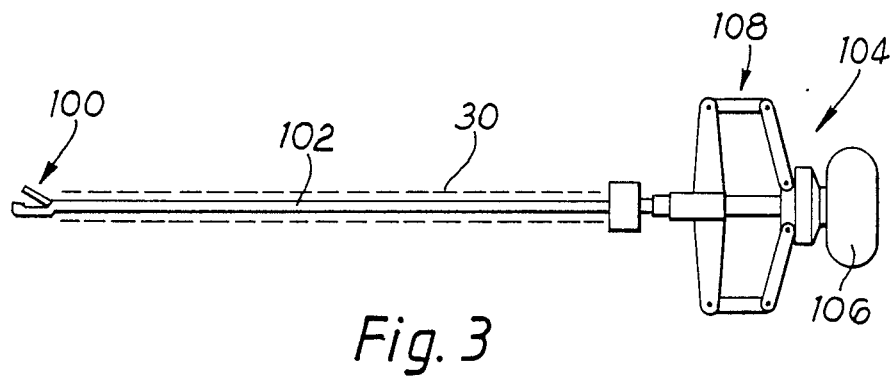
FIG. 3 shows schematically the applicator according to the present invention.

With reference now to FIGS. 1 and 2 of the drawings the known applicator comprises first and second portions 10, 20 joined by a screw threaded engagement 22. The first portion 10 carries an operating head 12 operated by a push rod (not shown), the push rod being pushed by the action of a movable handle 24 on the second portion 20 which is operated against a static handle 26.

The applicator is assembled through a laparoscope 30 (shown dotted) of known design by screw threading engagement of the two portions 10, 20. Each portion is inserted at opposite ends of the laparoscope and the screw thread engagement 22 is made in the centre of the laparoscope. The laparoscope is, in use, inserted into a cannula 40 which is inserted by a surgeon into patient.

The laparoscope and cannula are as small in diameter as possible in order to facilitate entry into the body of a patient. Therefore the applicator is made as small as possible in diameter to conform to and pass through the internal diameter of the laparoscope.

In use, the laparoscope 30 is inserted into the cannula 40 after loading the applicator with a clip 60 (FIG. 2). The applicator is partially closed to enable the clip to pass through the cannula.

The applicator of FIG. 1 has a number of disadvantages. The first is due to the narrow diameter of the joint 22 because to produce a smooth tube one of the portions 10, 20 is externally threaded to fit inside the other tube portion. Because of the small diameters involved the wall thickness of the tubes is thin and the tubes are weakened by the threading operation thereby creating two problems. Firstly the tubes may break causing the applicator to become useless and secondly there is a possibility, because of the fine thread necessary for cross threading to occur—especially within the inner confines of the laparoscope where it is impossible for the operator to observe the accuracy of the connection. Thirdly there is a possibility of bending occurring at the joint thereby causing misalignment of the handle and the clip.

If the connection is made in a cross thread then the operator will not know and the subsequent operation of the applicator may not close the clip completely thereby resulting in an unsuccessful operation.

The operating rods (not shown) are joined at or near to the joint 22 by a ball and socket arrangement which effectively allows movement of the handle 24 to both push and pull the rods thereby opening and closing the operating head 12. This is essential for manoeuvring the clip held within the head 12. This ball joint arrangement is prone to wear over a prolonged life of the applicator and such wear can result in an incomplete closure of the operating head thereby leading to failure of the operation.

For efficient operation of the applicator the orientation of the operating head and the handle should be the same so that the operator can "see" the orientation of the head 12 and hence of the clip 60 carried by the head. With the screw thread arrangement 22 the use of the applicator over a period will cause the threads to wear resulting in misalignment of the handle 24 and head 12. This can cause difficulties for the operator.

To enable the clip 60 to be passed through the cannula the applicator is used to partially close the clip 60 as shown in FIG. 2. If too much pressure is applied then the clip 60 may be partially engaged and, when the applicator has passed through the cannula and the pressure on the clip is released the clip, if partially held closed, may fall out of the operating head 12 and become lodged in the patients body requiring retrieval. This is obviously undesirable.

With reference to FIGS. 3 to 9 the applicator of the present invention seeks to overcome the above disadvantages whilst also providing further advantages.

The applicator comprises an operating head 100 connected into a first portion 102 which is continuous throughout the laparoscope 30 (shown dotted) and which is joined to a second handle portion 104 at the opposite end of the laparoscope.

The operating handle 104 (FIG. 4) comprises a knob 106, for holding, and a caliper arrangement 108 which operates a central plunger 110 via its rear operating levers 112, 114 which have respective projections 116, 118 co-operating with shoulders 120, 122 on plunger 110 to produce by virtue of the leverage ratio generated by the position of pivots 124, 126 a very large force on the plunger 110. In an alternative embodiment plunger 110 may be provided with a gear teeth rack (not shown) on both sides co-operating with pinions (not shown) on the ends 116, 118 of levers 112, 114 to drive the plunger 110 in a known rack and pinion arrangement.

The front arms 128, 130 of caliper 108 slide on a sleeve 132 mounted on the barrel 134 of the handle. The plunger 110 is spring urged into the non-operating position as shown by a coil spring 136.

Figure 5:
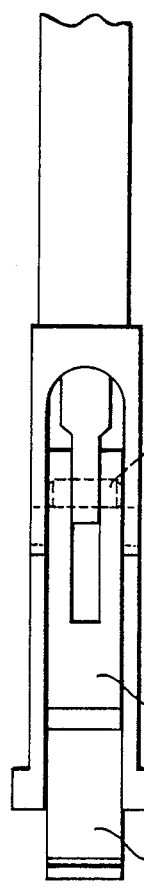
FIG. 5 shows the operating head of the applicator of FIG. 3 in plan view.
Figure 6:
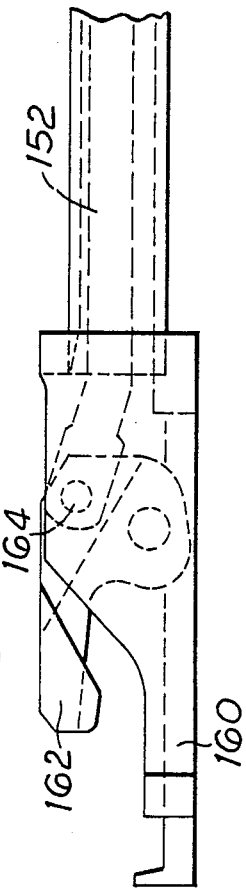
FIG. 6 shows the operating head of FIG. 5 in side elevation and partial cross-section.
Figure 7:
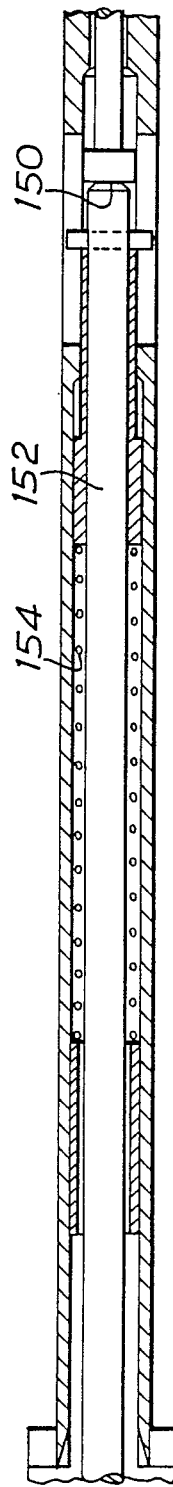
FIG. 7 shows a portion of the barrel of the applicator nearest the operating head in cross-section.
Figure 8:
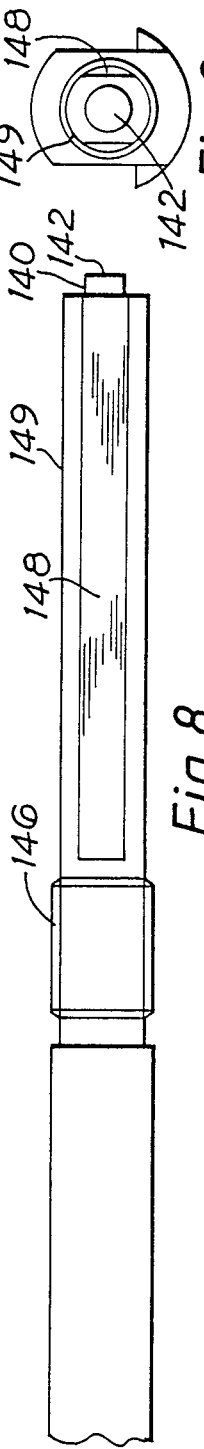
FIG. 8 shows a portion of the barrel of the applicator of FIG. 3 nearest the operating handle.
Figure 9:
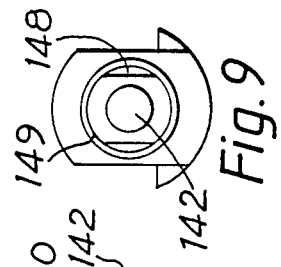
FIG. 9 shows an end elevation of FIG. 8.

The plunger 110 terminates as shown at 138 and in operation co-operates with the end 142 of an elongate push rod 140 (see FIG. 8). The push rod 140 operates via linkages which are shown in FIGS. 5 to 7 to cause the jaws of the operating head to be closed.

Figure 4:
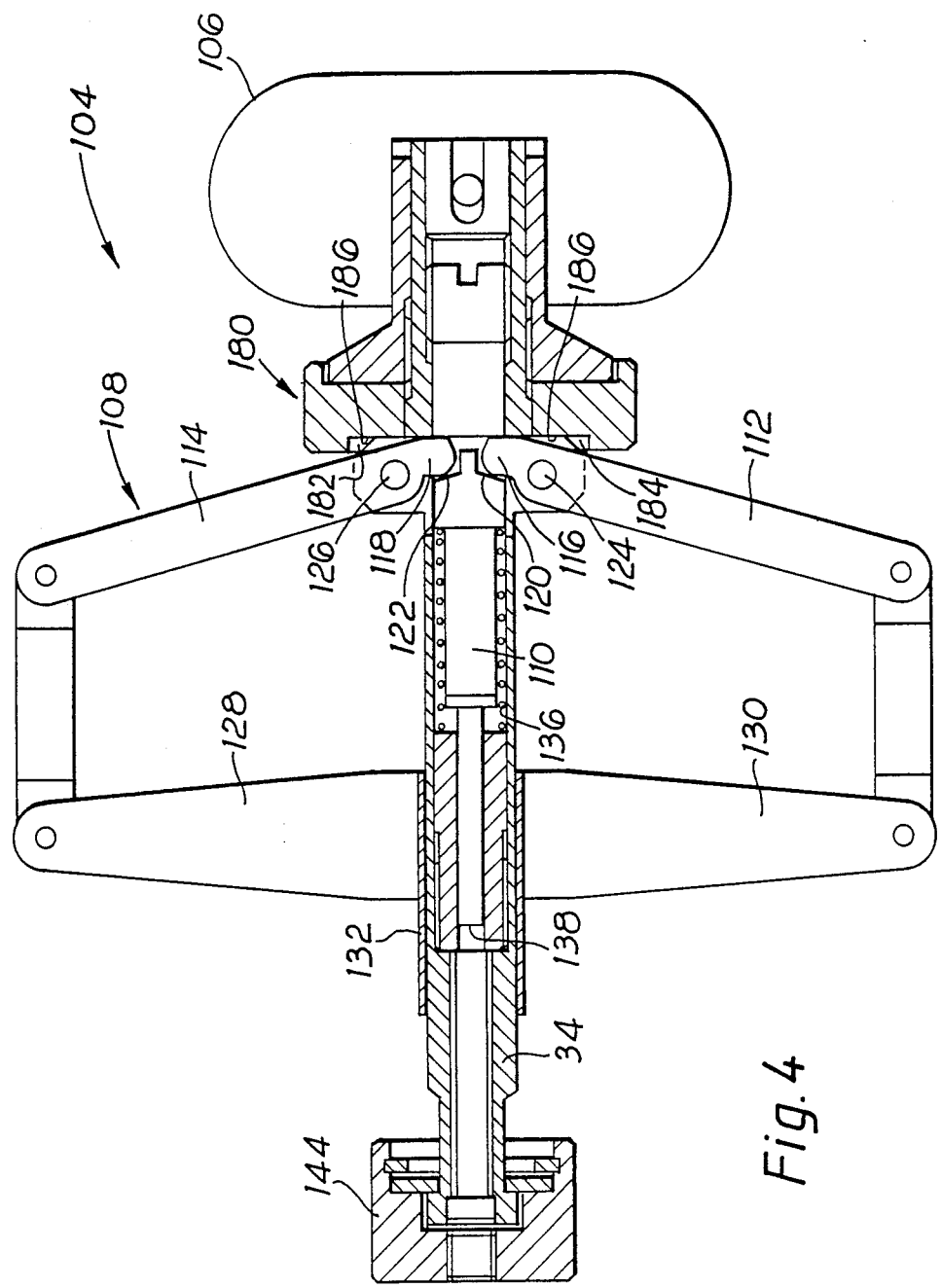
FIG. 4 shows the operating handle of the applicator of FIG. 3 in greater detail in side elevation and in partial cross-section.

With reference to FIGS. 4 and 8 the first portion 102 is joined to the second portion 104 by a screw threaded arrangement comprising a captive nut 144 which screws onto a screw thread 146 and in which the two portions are aligned in correct orientation by a chamfered portion 148 formed on the barrel portion 149. Thus the first and second portions can only be assembled in the alignment set by the chamfered portions (or 180° out of alignment in which case the operator can easily turn the applicator over).

The push rod 140 is continuous down the narrow section of first portion 102 and terminates (FIG. 7) at 150 where it is operative to drive an operating rod 152 which is spring urged by spring 154 into the nonoperative position for the operating head 100. The operating head (FIG. 6) comprises a static (bottom) jaw 160 and a movable (upper) jaw 162 pivotally operated about pivot 164 by operating rod 152. The jaw 162 is therefore operable by caliper arrangement 108 via rods 110, 140 and 152 and returned by spring 154 to its nonoperative position.

In FIG. 2 the head 100 is shown holding a clip 60 in the correct position to pass down the cannula. If the clip 60 is squeezed too tightly it may partially lock and the clip may fall out of the jaw. The handle arrangement of the present applicator provides a stop means as shown at 180 to enable the partial closure position to be positively maintained. The stop means comprises a captive but rotatable knurled circular nut 180 which has shoulders 182, 184 which are present over only a portion of the front surface 186 of the nut. The nut can be turned between two positions. In the first position the shoulders 182, 184 are not in alignment with the rear arms 112, 114 of caliper 108 and the rear arms are able to be moved fully backwards. In the second position the shoulders 182, 184 are in alignment with the arms 112, 114 and the rearward movement of the caliper is restricted. By careful choice of the dimensions of the shoulders this rear movement can be made to exactly conform to the required partial closure position shown in FIG. 2. Accidental further pressure on calipers 108 cannot then be transferred to the clip 60. When the clip 60 has passed safely down the cannula the "safety" nut 180 can be turned to the fully operative position for clip fixture.

The applicator shown in FIGS. 3 to 9 has many advantages. All drive rods are "flat" ended thereby providing good pressure to the head 100 and wear because of shaped ends. The alignment of head and handle is assured. There is no problem in ensuring that the two portions are correctly assembled and not cross threaded. Because the thread on portion 146 can be the full diameter of the barrel of first portion 102 this can be as strong as possible commensurate with the size of the applicator.

Figure 10:
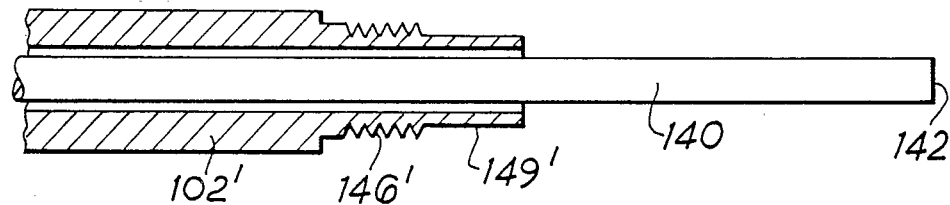
FIG. 10 shows a modification of FIG. 8 illustrating a further embodiment;.

With reference now to FIG. 10 an alternative embodiment is shown which is particularly advantageous for applicators which can have a larger diameter due to the presence of a larger hole through the cannula. This is especially obtainable where the viewing means is inserted via a separate cannula thereby leaving the whole diameter of the "applicator cannula" free for the applicator.

In this case the wear on the screw threads 146' is reduced because the threads 146' are of a larger diameter and may also be made much stronger because the tub forming the first portion 102' may be much thicker walled. Because of the extra strength possessed by the modified thread 146' the handle 104 can merely be screwed directly onto the portion 102' by means of a static female thread (not shown) instead of the captive nut 144. The alignment of the handle and operating head 100 can be by careful design of the screw threads and will be maintained during the life of the applicator because of the extra strength in screw thread 146' and the female thread (not shown) on handle 104.

Figure 11:
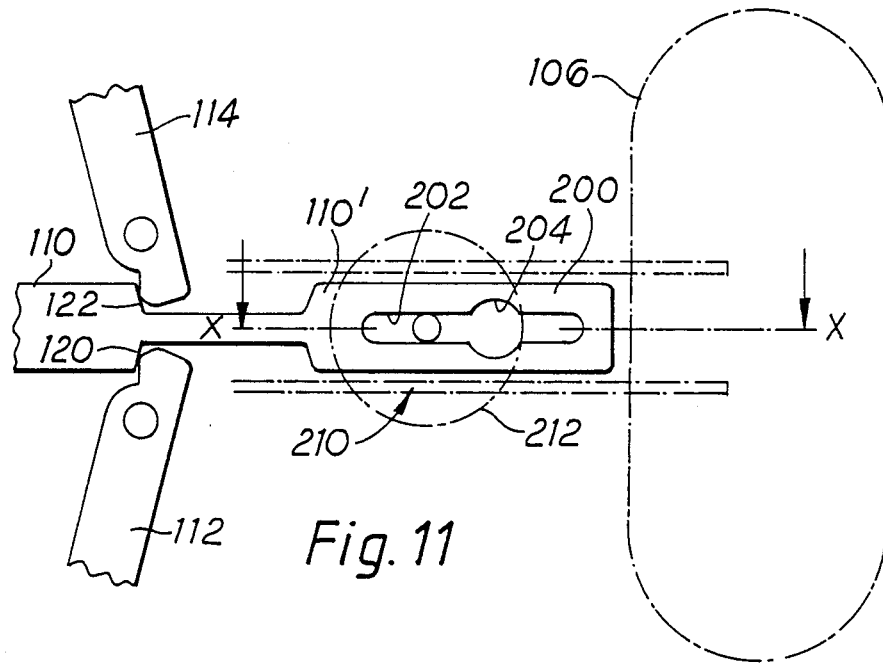
FIG. 11 shows a modification of a portion of FIG. 4 illustrating a further stop means.
Figure 12:
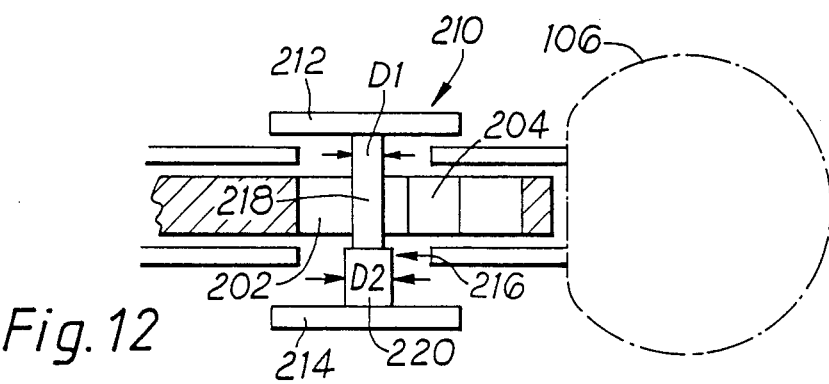
FIG. 12 shows a partial cross-section of FIG. 11 on line X—X.

With reference now to FIGS. 11 and 12, a portion of the handle 104 is sown. The levers 114, 116 are shown again operating on shoulders 120, 122 to move plunger 110 to force jaw 162 shut.

In this embodiment plunger 110 is modified and includes a continuation portion 110' which slides in the handle together with plunger 110. Portion 110' may preferably be formed integrally with plunger 110 and comprises a rod portion 200 with a slot 202 milled or moulded therethrough. In a generally central position in slot 202a a larger diameter hole 204 is formed.

A button 210 is operable in two directions by respective flat portions 212, 214 and has a stepped joining rod 216 with a small diameter (D1) portion 218 and a larger diameter (D2) portion 220.

The operation of the button 210 is as follows. In the position shown in FIG. 12 plunger 110 is free to move over the whole length of slot 202. When the portion 110' has moved such that the larger diameter hole 204 is in line with the rod 216 then, if required button 210 may be operated by pressing disc 214 to push larger diameter portion 220 into hole 204. In this position plunger 110 is locked against movement in either direction. The movement of plunger 110 at this position is such that a sterilisation clip inserted into operating head 12 will be held in a semi-closed position by upper jaw member 162 in such a manner that upper jaw member 162 will be substantially parallel with the lower jaw member thereby allowing passage of head 12 down the cannula without any possibility of any full pressure being applied to the clip. Once inserted through the cannula button 210 can be operated in the reverse direction by pressing disc 212 to once again allow free movement of the operating head 12.

I claim:

1. An applicator for a sterilization clip comprising a first portion and a second portion, the first portion including an operational handle and the second portion including an elongate tube for passage completely through a laparoscope and including means for engageably connecting the first and second portions at the handle end of the laparoscope, means for locking the alignment of said operational head and handle, the second portion also including an operational head, said operational head including jaw means for holding a sterilization clip, the operational handle being operative to close said jaw means via operating rod means guided within said elongate tube, said operational handle including mechanical advantage leverage means for imposing forces on said operating rod means to close said jaw means to effect closure of a sterilization clip when the latter is fitted within the jaw means, said applicator further comprising stop means operatively connected within the operational handle and comprising means for restricting movement of the operational handle, the stop means being operative after partial closure of the jaw means by the operational handle to prevent opening of the jaw means past a specified partially closed position to thereby retain within the jaw means a partially closed sterilization clip and to retain the jaw means in a partially closed position to allow the applicator to be fed through a cannula into the interior of a patient.

2. An applicator as claimed in claim 1 in which the engagement is by screw thread means.

3. An applicator as claimed in claim 2 in which the means for locking the alignment is by shaping the engagement end of the second portion in a manner to engage in a non-rotatable manner a shaped end of the first portion.

4. An applicator as claimed in claim 1 in which the stop means comprises a rotatable member with shoulder means operable in a first position to prevent movement of the operational handle past the specified partially closed position and operable in a second position to allow full operational movement of the handle.

5. An applicator as claimed in claim 1 in which the stop means comprises a button arrangement operable in a first position to prevent movement of the operational handle past the specified partially closed position and operable in a second position to allow full operational movement of the handle.

6. An applicator as claimed in claim 1 in which the operating rod means includes a first operating push rod within the first portion and a second operating push rod within the second portion, the first and second push rods having respective abutting flat ends providing positive drive for the operational head.

7. An applicator as claimed in claim 6 in which the first operating push rod is provided with attachment means for the attachment of a return spring, the return spring being operative to urge the first push rod against the second push rod.

* * * * *